(12) United States Patent
Jiang et al.

(10) Patent No.: US 7,270,994 B2
(45) Date of Patent: Sep. 18, 2007

(54) *LACTOBACILLUS CASEI* BD-II STAIN AND USED TO REDUCE BLOOD CHOLESTEROL

(75) Inventors: Nengqun Jiang, Shanghai (CN); Benheng Guo, Shanghai (CN); Liguo Sun, Shanghai (CN)

(73) Assignee: Shanghai Bright Dairy & Food Co. Ltd., Shanghai (CN)

( * ) Notice: Subject to any disclaimer, the term of this patent is extended or adjusted under 35 U.S.C. 154(b) by 0 days.

(21) Appl. No.: 10/559,067

(22) PCT Filed: Aug. 4, 2003

(86) PCT No.: PCT/CN03/00623

§ 371 (c)(1), (2), (4) Date: Nov. 30, 2005

(87) PCT Pub. No.: WO2004/106498

PCT Pub. Date: Dec. 9, 2004

(65) Prior Publication Data

US 2006/0127380 A1 Jun. 15, 2006

(30) Foreign Application Priority Data

May 30, 2003 (CN) .................................. 03128995

(51) Int. Cl.
*A01N 63/00* (2006.01)
*C12N 1/02* (2006.01)
*C12N 1/20* (2006.01)

(52) U.S. Cl. .............................. 435/252.9; 424/93.45; 435/261; 435/856

(58) Field of Classification Search ..................... None
See application file for complete search history.

(56) References Cited

FOREIGN PATENT DOCUMENTS

| CN | 1255943 A | 6/2000 |
|---|---|---|
| JP | 10229841 A | 9/1998 |
| WO | WO9823727 A1 | 6/1998 |

*Primary Examiner*—Sandra E. Saucier
*Assistant Examiner*—Deborah K. Ware
(74) *Attorney, Agent, or Firm*—Crowell & Moring LLP

(57) ABSTRACT

The invention disclosed a kind of *lactobacillus casei* Bd-II, the accession number of the deposit of which is CGMCC NO.0849, and also disclosed a use of it for reducing blood lipid level. Further, a composition for reducing blood lipid level containing it and an acceptable carrier is disclosed. The carrier can be skimmed milk.

5 Claims, No Drawings

LACTOBACILLUS CASEI BD-II STAIN AND USED TO REDUCE BLOOD CHOLESTEROL

FIELD OF THE INVENTION

The invention relates to a new strain of *lactobacillus* and its use for reducing blood lipid level.

BACKGROUND OF THE INVENTION

There are a lot of beneficial microbial populations in the intestinal tracts of human beings and animals as well as in the traditional fermented food etc., playing important physiological roles in digestion & absorption of nutrition, body growth & development, immunity & antagonism and so on. In recent years, microecologists have found that probiotics community such as *lactobacillus, bifidobacterium* and *enterococcus* etc. are directly related to the metabolism of cholesterol. Many researches performed in-vitro and in-vivo abroad have substantiated that some probiotic *lactobacillus* can lower serum cholesterol level of human beings and animals. However, lots of such bacterial resources in Chinese traditional food, which have not yet discovered by western scientists, need to be exploited further.

PURPOSE OF THE INVENTION

Based on the above topic, the inventor selected the microbial populations in pickle and salt-preserving clover (Chinese traditional food) as target and applied high cholesterol culture medium, then screened probiotic *lactobacillus* which can reduce cholesterol level, and further investigated its use for regulating blood lipid.

As a result, the purpose of the invention is to provide a kind of *lactobacillus casei* Bd-II; The other purpose of the invention is to provide the use of the said *lactobacillus casei* Bd-II for reducing blood lipid level.

SUMMARY OF THE INVENTION

The preparation procedure of *lactobacillus casei* Bd-II according to the invention is as follows: pickle juice or clover juice is preserved by refrigeration as sample whose pH is determined later, then inoculated on MRS plate (purchased from Merck) where total colonies after cultivation will be counted. The sample obtained above is collected, then soaked and mixed uniformly with pH6.8 PBS buffer and performed by gradient dilution according to the above measured value.

100 μL of solution with appropriate dilution (about 100 bacteria per mL) is sucked and then smeared on LBS plate to culture.

Typical colony acquired above is picked to inoculate on MRS plate for further purification. Ideal single colony on MRS plate above is picked to inoculate into MRS liquid medium for enrichment so as to acquire *lactobacillus* strain to be frozen.

By model in-vitro probiotic being capable of decreasing cholesterol is screened primarily from the fresh strain of *lactobacillus* above (USMAN and A.HOSONO. Bile tolerance, taurocholate deconjugation, and binding of cholesterol by *lactobacillus gasseri* strains. J. Dairy Sci. 1999 82:243-248.), and then *lactobacillus casei* Bd-II is acquired through species identification. The microbiological characteristics of *lactobacillus casei* Bd-II are shown in Table 1.

TABLE 1

Microbiological characteristics of *Lactobacillus Casei* Bd-II

| Test Item | Result |
| --- | --- |
| Gram staining | Positive |
| Cell morphology | Rod shape |
| Gem formation | − |
| Catalase | − |
| Oxidase | − |
| Growth in air | + |
| Facultative anaerobic growth | + |
| O/F test | fermentation |
| Lactic acid production | + |
| Gas production of carbohydrate | |
| Glucose | − |
| Sodium gluconate | + |
| Acid production of carbohydrate | |
| Glucose | + |
| Sodium gluconate | + |
| Cellobiose | + |
| Arabinose | − |
| Sucrose | + |
| Acid production of carbohydrate (continued) | |
| Mycose | + |
| Xylose | − |
| Fructose | + |
| Ribose | + |
| Raffinose | + |
| Lactose | + |
| Melizitose | + |
| Salicin | + |
| Rhamnose | − |
| Esculin | + |
| Mannose | + |
| Mannitol | + |
| Maltose | + |
| Sorbitol | + |
| Melibiose | − |
| Galactose | + |

All of the above operations are performed under aseptic environment.

In addition to the beneficial effects of common *lactobacillus, lactobacillus casei* Bd-II according to the invention can play an auxiliary role in lowering the concentration of serum cholesterol of human being provided it is used for regulating blood lipid, such as exploiting functional milk product or serving as supplementary agent of foods.

By means of the following examples, we will describe the invention in detail. The following examples are only for explanation and the invention is not limited to the disclosed embodiment.

On Dec. 6, 2002 *Lactobacillus casei* Bd-II according to the invention was deposited at China General Microbiological Culture Collection Center (CGMCC), which is located at No. 13, Beiyitiao, Zhongguancun, Haidian District, Beijing, China; and was given the accession number of the deposit CGMCC NO. 0849.

DESCRIPTION OF THE INVENTION

EXAMPLE 1

Samples Collection

The samples are:
Pickle juice: obtainable by homogenizing the leaves and the juice of cabbage pickle;

Clover juice: obtainable by homogenizing 5 g of salt-preserving clover collected from a farmer of Tianping Mountain, Suzhou and 10 mL of sterile water.

EXAMPLE 2

Lactobacillus Screening

The samples obtained above are put into sterile screw bottles which will be screwed tightly, and preserved by freezing at 4° C. pH values of the pickle juice and the clover juice are determined during 24 hours. Then the samples are inoculated on MRS plate where total colonies after cultivation will be counted, and finally are treated by the following step.

EXAMPLE 3

LBS Plate Isolation

Pickle juice and clover juice are sucked and performed by gradient dilution with PBS buffer (pH 6.8) under aseptic environment according to the pH values determined in Example 2. 100 μL of solution with appropriate dilution (about 100 bacteria per mL) is sucked to smear on LBS plates. LBS plates are put inversely into an anaerobic incubator, and then cultured at 37° C. for 36~72 hours. The colony growth is observed during the cultivation. Finally after the cultivation the plate is preserved by freezing at 4° C.

EXAMPLE 4

Strain Test under Microscope

Under aseptic environment, typical colony acquired in Example 3 is picked with inoculating loop to smear on slide for gram staining. Thallus morphology is observed by oil microscope in order that the bacterium of gram staining positive can be picked as target colony.

EXAMPLE 5

Strain Purification on Plate

Under aseptic environment, target colony defined preliminarily in Example 4 is picked with inoculating loop to smear on MRS plates and isolated through plate streaking, then cultured for 24~36 hours at 37° C. inversely in anaerobic incubator. Single colony is picked to test under microscope until the strain has been purified assuredly.

EXAMPLE 6

Enrichment Procedure of Strain

Ideal single colony acquired in Example 5 is picked to inoculate into 1 mL of MRS liquid, and cultured statically at 37° C. for about 24 hours. Then the culture is inoculated into fresh MRS liquid with 1% of inoculum size and cultured statically at 37° C. for 24 hours. Finally the culture obtained above is enriched in MRS liquid twice and the culture liquid acquired is preserved at 4° C.

EXAMPLE 7

By in-vitro Model Preliminary Screening of Probiotic that can Decrease Cholesterol 10 mL of high cholesterol culture medium MRSO-CHOL which contains sterile egg yolk as the source of cholesterol is added into 1 5 mL of sterile centrifuge tube. The fresh strain acquired in Example 6 is inoculated into the tube with 1% of inoculum size, and then cultured for 24 hours at 37° C. The culture medium after cultivation is separated by centrifugation at 12,000×g for 10 minutes. The concentration of cholesterol in the supernatant is measured according to the methods as how cholesterol is determinied by o-phthalaldehyde. With MRSO-CHOL culture which is not inoculated as a control, decrease rate of cholesterol of each strain tested is calculated respectively (S. E. Glliland, C. R. Nelson, C. Maxwell. Applied and Enviromental Microbiology, 1985, 49:377~381.). Therefore, the strain that can decrease cholesterol obviously can be picked out. The results are shown in Table 2.

The formula for calculating decrease rate of cholesterol is:

$$D = \frac{C - A}{C} \times 100\%$$

Wherein, "A" represents $OD_{550\,nm}$ [light absorption degree at the wavelength of 550 nm (namo)] of fermentation supernatant of each strain tested;

"C" represents $OD_{550\,nm}$ of control;

"D" represents decrease rate of cholesterol.

TABLE 2

Results of Preliminary Screening of Probiotic Lactobacillus being Capable of Decreasing Cholesterol

| Decrease Rate of Cholesterol (%) | Numbers of the Strain (Strain) | Ratio (%) | Pickle | Source Salt-preserving clover |
|---|---|---|---|---|
| >40 | 6 | 9.09 | 4 | 2 |
| 30~40 | 9 | 13.64 | 5 | 2 |
| 20~30 | 13 | 19.70 | 2 | 8 |
| <20 | 38 | 57.28 | 12 | 16 |

Wherein, Bd-II has a relatively high decrease rate of cholesterol, up to 45.17%, and correspondingly, the decrease of the amount of cholesterol is 231.95 μg/mL. In addition, there are another 5 strains having decrease rate of cholesterol more than 40%.

EXAMPLE 8

Bd-II Strain Identification

Identified by Institute of Microbiology, Chinese Academy of Sciences (IMCAS), the microbiological characteristics of Bd-II are shown in Table 1.

EXAMPLE 9

Preparation of Bacterial Suspension

*Lactobacillus casei* Bd-II (CGMCC No. 0849) according to the invention is inoculated into 10% of skimmed milk, and cultured statically at 37° C. for 16 hours. After cultivation the amount of cell in the culture is counted. Therefore, the culture is diluted and suspended appropriately with skimmed milk according to the counting results above, so that the different cell concentration shown in Table 3 is obtained. The preparation of dead bacterial suspension of Bd-II is as follows: suspending Bd-II into skimmed milk with the result that the cell concentration is $10^8$ cfu/mL (bacteria number per mL), then puting the skimmed milk containing Bd-II into water bath at 100° C. for 15 minutes, finally cooling the sample obtained above and preserving it in refrigerator for further use.

Functional Experiment on Decreasing Cholesterol in Serum (in vivo Animal Experiment)

Animal model has been widely used in the functional experiment of probiotic *lactobacillus* which can reduce serum cholesterol (Zheng Jianxian, Functional Food(Volume III), Beijing: China Light Industry Press, 1999. 9. 408-412). Feed with high lipid and high cholesterol can induce metabolism disorder of animal fat and change the blood lipid level, for example it can increase the concentration of TC, TG and LDL-C in serum, while decrease the concentration of HDL-C in serum. Functional experiment on decreasing cholesterol in serum is generally designed as follows: feeding animal with feedstuff containing high cholesterol, as well as the experimental sample, and then determining the effect of experimental sample on animal blood lipid through measuring lipid concentration in animal serum.

Probiotic *lactobacillus* screened according to the invention is *lactobacillus casei* Bd-II (CGM CC No.0849), which has relatively great ability to reduce cholesterol in-vitro.

In the invention, SD mice are used as experimental animal. Cholesterol, lard and pig bile salt are added into routine feedstuff in the amounts of 1%, 5% and 0.25% respectively, to induce hypercholesterolemia of SD mouse. At the same time, SD mice are fed with skimmed milk containing *lactobacillus casei* suspension. Finally, blood lipid index such as cholesterol in serum of SD mice is measured to determine whether the strain has the effect of reducing cholesterol in serum.

1. Experimental Animal and Condition of Laboratory Animal Housing 40 male SD mice (8 weeks old) are fed with routine feedstuff for 3 days, divided into 5 groups randomly so as to 8 mice each group. Each group is kept and fed in cage individually.

Condition of laboratory animal housing is: at the temperature of 22±2° C.; at humidity of 56±5%; replacing sawdust twice to thrice each week; and controlling 12 hours for illumination and 12 hours for darkness.

Feedstuff is: routine feedstuff supplied by Shanghai Laboratory Animal Center, Chinese Academy of Sciences; and feedstuff containing high cholesterol which is obtained by adding cholesterol, lard and pig bile salt into routine feedstuff in the amounts of 1%, 5% and 0.25% respectively, and which is produced by Shanghai Laboratory Animal Center on commission. All feedstuff is sterilized by radiation before entering laboratory animal housing.

2. Method for Functional Animal Experiment of Probiotic *lactobacillus* Bd-II (1) Animal Grouping and Feeding Plan 40 SD mice are divided into 5 groups randomly, and fed with different feedstuff and bacteria suspension, shown in Table 3 in detail.

TABLE 3

Animal Grouping and Feeding Plan

| Grouping[a] | Daily feeding[b] | Intragastric administration; 3 mL/mouse/day |
|---|---|---|
| 1. blank control | routine feedstuff + water | water |
| 2. high lipid control | high lipid feedstuff + water | water |
| 3. high lipid SKM control | [c]high lipid feedstuff + water | SKM |
| 4. live Bd-II | high lipid feedstuff + water | SKM suspended with $2.5 \times 10^8$ cfu/mL of live Bd-II |
| 5. dead Bd-II | high lipid feedstuff + water | SKM suspended with $2.5 \times 10^8$ cfu/mL of dead Bd-II | note:
[a]8 SD mice each group
[b]feeding for consecutive 21 days
[c]SKM - sterile 10% of skimmed milk (2) Daily Management of Animal and Feeding SD mice are randomly divided into Group 1-5 as shown in Table 3. Mice of Group 2-5 are fed with high lipid feedstuff except those of Group 1 as blank control, which are fed with routine feedstuff. SD mice are fed with 3 mL/mouse/day of feedstuff according to scheme in Table 3, by intragastric administration at 8 a.m. every day.

(3) Collection of Mouse Serum and Assay of Blood Lipid Concentration

After feed for 21 consecutive days, the mice are on a diet for 12 hours, and then anesthetized deeply with ether. Theirs eyeballs are picked to extract blood, and put into sterile centrifuge tubes, then separated by centrifugation at 3000×g for 10 minutes. Finally serum after centrifugation is collected and sent to Testing Center of Shanghai Huashan Hospital to assay TC, TG, HDL-C and LDL-C.

(4) Statistical Analysis

The data in the same group is performed by single factor analysis of variance, while the data among different groups is performed by t test. If $p<0.05$, it represents that the data have statistical difference; if $p<0.01$ and $p<0.001$, it represents that the data have significant statistical difference.

3. Analysis of Results

After feed for 21 consecutive days, the mice are on a diet for 12 hours. The mice serum is collected and sent to Shanghai Huashan Hospital to assay TC, TG, HDL-C, and LDL-C. Then the AI (atherosclerosis factor) is calculated and shown in Table 4 in detail.

TABLE 4

Results of Assaying Mice blood lipid

| Group | TC(mmol/L) | TG(mmol/L) | HDL(mmol/L) | LDL(mmol/L) | AI (LDL/HDL) |
|---|---|---|---|---|---|
| 1 | 1.4 ± 0.29*** | 0.68 ± 0.20* | 1.02 ± 0.21* | 0.38 ± 0.16*** | 0.38 ± 0.18*** |
| 2 | 2.56 ± 0.23 | 0.97 ± 0.19 | 0.79 ± 0.04 | 1.77 ± 0.20 | 2.23 ± 0.19 |
| 3 | 2.44 ± 0.36 | 0.90 ± 0.10 | 0.92 ± 0.10 | 1.52 ± 0.41 | 1.70 ± 0.58 |
| 4 | 1.94 ± 0.40** | 0.91 ± 0.32 | 0.83 ± 0.17 | 1.11 ± 0.34** | 1.38 ± 0.52** |
| 5 | 2.03 ± 0.48* | 0.82 ± 0.27 | 0.84 ± 0.09 | 1.19 ± 0.45 | 1.42 ± 0.50** |

Wherein, "*" represents having statistical difference compared with Group 2 ($P < 0.05$);
"**" represents having significant statistical difference compared with Group 2 ($P < 0.01$);
"***" represents having significant statistical difference compared with Group 2 ($P < 0.001$).

As shown in Table 4, TC, LDL and AI have significant statistical difference and TG & HDL have statistical difference between blank control group (Group 1) and high lipid control group (Group 2), which indicate that hyperlipemia animal model has been established successfully.

As can be seen from Table 4 that there is no statistical difference between high lipid skimmed milk control group (Group 3) and high lipid control group (Group 2), which indicate that skimmed milk culture medium solely has no effect on decreasing blood lipid.

Also as can be seen from Table 4 that compared with high lipid group(group 2), live Bd-II in live Bd-II group (Group 4) can enormously reduce TC, LDL and AI, but can't reduce TG and HDL so that the data of TG and HDL have no statistical difference, which indicate that Bd-II has remarkable function of reducing blood lipid, therefore it can reduce the risk of cardiovascular disease. Compared with high lipid group(group 2), dead Bd-II in dead Bd-II group (Group 5) can decrease TC obviously and AI tremendously, but can't decrease TG, HDL and LDL so that the data of TG, HDL and LDL have no statistical difference, which indicate that dead Bd-II also can lower blood lipid level so that it can reduce the risk of cardiovascular disease.

What is claimed is:

1. A biologically pure strain of *lactobacillus casei* Bd-II, the accession number of the deposit of which is CGMCC No. 0849.

2. A method for reducing blood lipid level comprising administering *lactobacillus casei* Bd-II, the accession number of the deposit of which is CGMCC No. 0849.

3. The method of claim 2 wherein administering comprises administering a therapeutically effective amount of said *lactobacillus casei* Bd-II, the accession number of the deposit of which is CGMCC No. 0849.

4. A composition for reducing blood lipid level, which comprises a blood-lipid-reducing amount of probiotic *lactobacillus casei* Bd-II the accession number of the deposit of which is CGMCC No. 0849, and a physiologically acceptable carrier.

5. The composition of claim 4 wherein the physiologically acceptable carrier is skimmed milk.

* * * * *